(12) United States Patent
Matsumura

(10) Patent No.: US 9,188,466 B2
(45) Date of Patent: Nov. 17, 2015

(54) BIOLOGICAL SAMPLE MEASURING DEVICE

(75) Inventor: Keisuke Matsumura, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 462 days.

(21) Appl. No.: 13/878,480

(22) PCT Filed: Sep. 20, 2011

(86) PCT No.: PCT/JP2011/005271
§ 371 (c)(1),
(2), (4) Date: Apr. 9, 2013

(87) PCT Pub. No.: WO2012/056628
PCT Pub. Date: May 3, 2012

(65) Prior Publication Data
US 2013/0197843 A1    Aug. 1, 2013

(30) Foreign Application Priority Data

Oct. 28, 2010    (JP) ................................. 2010-241646

(51) Int. Cl.
*G01D 18/00*    (2006.01)
*A61B 5/15*    (2006.01)
(Continued)

(52) U.S. Cl.
CPC .............. *G01D 18/00* (2013.01); *A61B 5/1411* (2013.01); *A61B 5/14532* (2013.01); *A61B 5/150022* (2013.01); *A61B 5/15105* (2013.01); *A61B 5/150259* (2013.01); *A61B 5/150786* (2013.01); *A61B 19/44* (2013.01); *G01N 33/48785* (2013.01); *A61B 5/157* (2013.01);
(Continued)

(58) Field of Classification Search
CPC ..................................................... G01D 18/00
See application file for complete search history.

(56) References Cited

U.S. PATENT DOCUMENTS

| 4,685,059 A | 8/1987 | Yamamoto |
| 5,246,858 A | 9/1993 | Arbuckle et al. |

(Continued)

FOREIGN PATENT DOCUMENTS

| JP | 60035245 | 2/1985 |
| JP | 6-506062 | 7/1994 |

(Continued)

OTHER PUBLICATIONS

Supplementary Partial European Search Report issued Jan. 29, 2014 in corresponding European Application No. EP 11835776.3.

(Continued)

*Primary Examiner* — Phuong Huynh
(74) *Attorney, Agent, or Firm* — Wenderoth, Lind & Ponack, L.L.P.

(57) ABSTRACT

This biological sample measuring device has a finger groove (6) provided in the short-side direction of a main body case (1) at a position that is closer to a sensor mounting portion (4) than a display section (5) on the rear side of the main body case (1). An interface unit (7) is provided on the front side portion of the main body case (1) corresponding to the finger groove (6). The interface unit (7) has an enter key (7*b*) and a plurality of cross keys (7*ca*), etc., disposed at a specific spacing around the outer periphery of the enter key (7*b*). The enter key (7*b*) is provided so that it protrudes farther than the cross keys (7*ca*), etc., on the front side of the main body case (1). A controller (13) performs a reset operation when a plurality of keys are pressed.

6 Claims, 20 Drawing Sheets

(51) Int. Cl.
*A61B 5/145* (2006.01)
*A61B 5/151* (2006.01)
*A61B 19/00* (2006.01)
*G01N 33/487* (2006.01)
*A61B 5/157* (2006.01)
*A61B 5/00* (2006.01)

(52) U.S. Cl.
CPC ...... *A61B 5/15142* (2013.01); *A61B 5/150358* (2013.01); *A61B 5/7475* (2013.01); *A61B 5/7495* (2013.01); *A61B 2019/442* (2013.01); *A61B 2560/0425* (2013.01); *A61B 2562/0295* (2013.01)

(56) References Cited

U.S. PATENT DOCUMENTS

| | | | |
|---|---|---|---|
| 5,281,395 A * | 1/1994 | Markart | G01N 21/8483 235/375 |
| 5,307,263 A | 4/1994 | Brown | |
| 5,685,319 A | 11/1997 | Marett | |
| 5,903,257 A | 5/1999 | Nishiumi | |
| 6,278,378 B1 | 8/2001 | Feiner et al. | |
| 7,077,328 B2 | 7/2006 | Krishnaswamy et al. | |
| 7,126,584 B1 | 10/2006 | Nishiumi | |
| 7,689,440 B2 | 3/2010 | Brown | |
| 7,765,111 B2 | 7/2010 | Brown | |
| 8,015,025 B2 | 9/2011 | Brown | |
| 8,024,201 B2 | 9/2011 | Brown | |
| 8,647,575 B2 | 2/2014 | Ohashi | |
| 2002/0060247 A1* | 5/2002 | Krishnaswamy | A61B 5/0002 235/472.01 |
| 2007/0094049 A1 | 4/2007 | Brown | |
| 2007/0118403 A1 | 5/2007 | Brown | |
| 2007/0118404 A1 | 5/2007 | Brown | |
| 2007/0118588 A1 | 5/2007 | Brown | |
| 2007/0118589 A1 | 5/2007 | Brown | |
| 2011/0223078 A1 | 9/2011 | Ohashi | |
| 2012/0185278 A1 | 7/2012 | Brown | |

FOREIGN PATENT DOCUMENTS

| | | |
|---|---|---|
| JP | 7-5109 | 1/1995 |
| JP | 8-506192 | 7/1996 |
| JP | 9-167050 | 6/1997 |
| JP | 10-0038879 | 2/1998 |
| JP | 2002-521692 | 7/2002 |
| JP | 2003-215086 | 7/2003 |
| WO | 2010/058815 | 5/2010 |

OTHER PUBLICATIONS

European Office Action issued Feb. 10, 2014 in corresponding European Application No. EP 11835776.3.

International Search Report issued Nov. 22, 2011 in International (PCT) Application No. PCT/JP2011/005271.

* cited by examiner

BIOLOGICAL SAMPLE MEASURING DEVICE

TECHNICAL FIELD

The present invention relates to a biological sample measuring device which measures blood glucose levels, lactic acid levels, and so forth in biological samples, for example.

BACKGROUND ART

Conventional biological sample measuring devices are configured as follows.

Specifically, a conventional biological sample measuring device comprises a main body case, a data reader and sensor mounting portion that are provided on a first end side in the lengthwise direction of the main body case, and a display section provided on the surface closer to the first end side in the lengthwise direction of the main body case (see Patent Literature 1, for example).

In the above configuration, when the conventional biological sample measuring device is used, first the user holds the second end side of the main body case and uses the data reader to read measurement technician ID data, patient ID data, and sensor ID data. Then, a sensor is mounted to the sensor mounting portion, after which the finger of the patient is pricked and the sensor is brought into contact with the pricked finger to supply blood to the sensor, so that the blood glucose level can be measured, for example.

CITATION LIST

Patent Literature

Patent Literature 1: Japanese Unexamined Patent Application Publication (Translation of PCT Application) No. 2002-521692

SUMMARY

A problem encountered with the above-mentioned conventional biological sample measuring device was that it was not easy to use.

Specifically, with the above-mentioned conventional biological sample measuring device, the reset operation, which was performed to return to a normal status when the program malfunctioned, was performed by sticking a pin into a small reset hole provided to the rear of the main body case. However, since this entailed working with a small reset hole, it could be a difficult job.

In view of this, it is an object of the present invention to provide an easy-to-use biological sample measuring device with which the user is prevented from accidentally carrying out a reset operation, while the reset operation can still be carried out by a simple manipulation.

To achieve the stated object, the present invention comprises a main body case, a data reader, a sensor mounting portion, a display section, a finger groove, an interface unit, and a controller. The data reader is provided on a first end side in the lengthwise direction of the main body case. The sensor mounting portion is provided on a second end side that is on the opposite side from the first end in the lengthwise direction of the main body case. The display section is provided to the surface on the first end side of the main body case. The finger groove is provided at a position that is more to the sensor mounting portion side than the display section on the rear side of the main body case, and is formed in the short-side direction of the main body case. The interface unit is provided at a position on the front side of the main body case corresponding to the finger groove, and has an enter key and a plurality of keys or buttons disposed at a specific spacing around the outer periphery of the enter key so that the enter key protrudes the farthest on the front of the main body case. The controller is connected to the interface unit and performs a reset operation when a plurality of keys or buttons are pressed at the same time.

Advantageous Effects

With the present invention, the reset operation is performed by simultaneously pressing a plurality of keys or buttons present around the outer periphery of the enter key, rather than using the enter key that protrudes farther on the front side of the main body case. Accordingly, an easy-to-use biological sample measuring device can be provided with which the user is prevented from accidentally performing a reset operation, but the reset operation can still be carried out by a simple manipulation.

DESCRIPTION OF EMBODIMENTS

A biological sample measuring device that measures blood glucose levels will be described through reference to the drawings, as an embodiment of the present invention.

Figure 1:
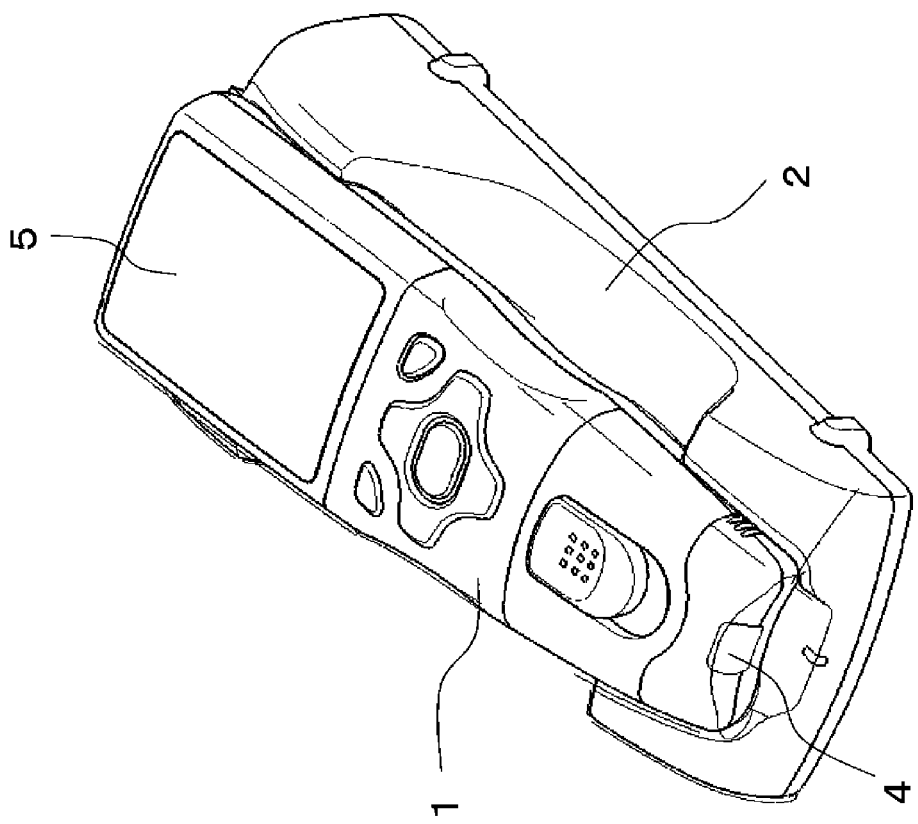
FIG. 1 is an oblique view of the configuration of the biological sample measuring device pertaining to an embodiment of the present invention.

As shown in FIG. 1, the biological sample measuring device in this embodiment comprises a main body case 1. The main body case 1 is mounted in a removable state on a cradle 2 that is open on its top face.

As shown in FIGS. 2 to 5, the lateral (width) direction of the main body case 1 is the short-side direction, and the longitudinal direction is the lengthwise direction. A barcode reader or other such data reader 3 is provided, for example, on a first end side of the main body case 1. A sensor mounting portion 4 is provided on a second end side that is on the opposite side from the first end of the main body case 1.

Figure 2:
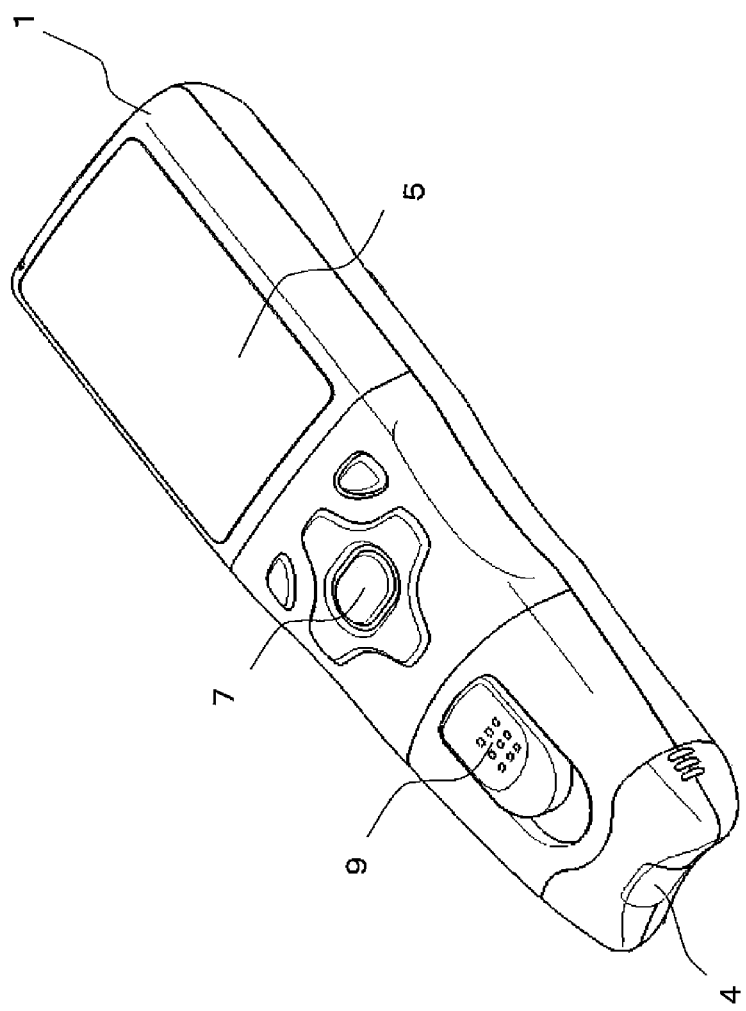
FIG. 2 is an oblique view of the front side of the biological sample measuring device in FIG. 1.
Figure 3:
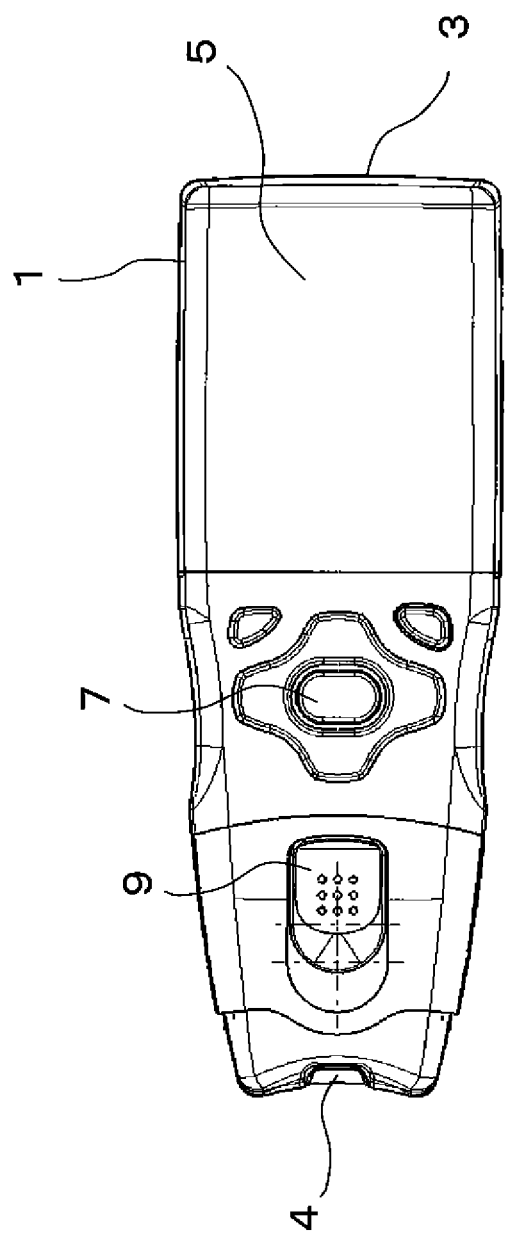
FIG. 3 is a top view of the biological sample measuring device in FIG. 1.

As shown in FIGS. 2 and 3, a display section 5 that is rectangular and longer in the lengthwise direction is provided to the surface on the first end side of the main body case 1.

Figure 4:
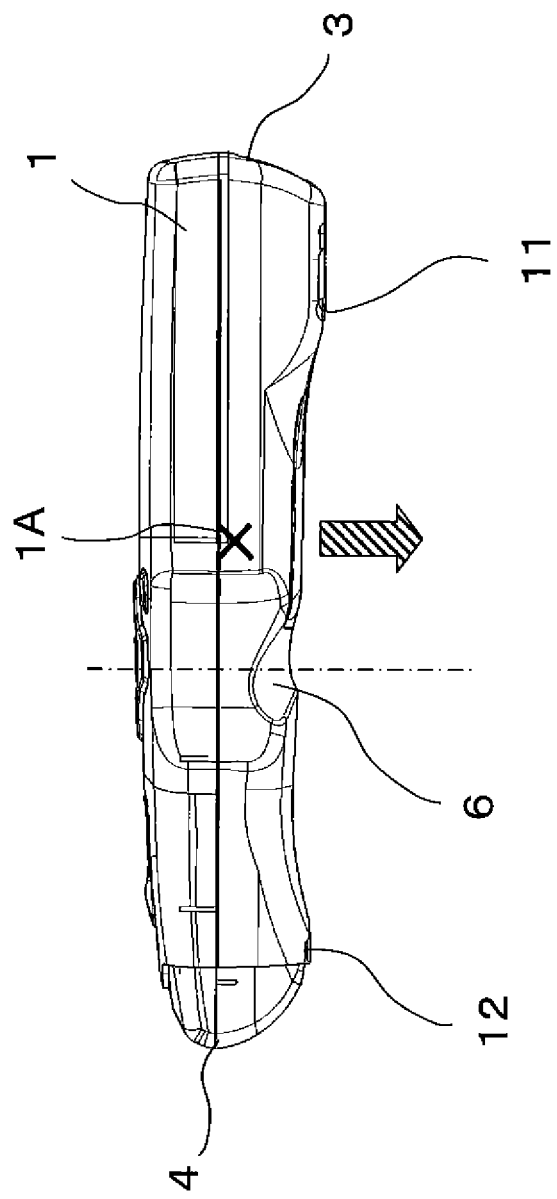
FIG. 4 is a side view of the biological sample measuring device in FIG. 1.
Figure 5:
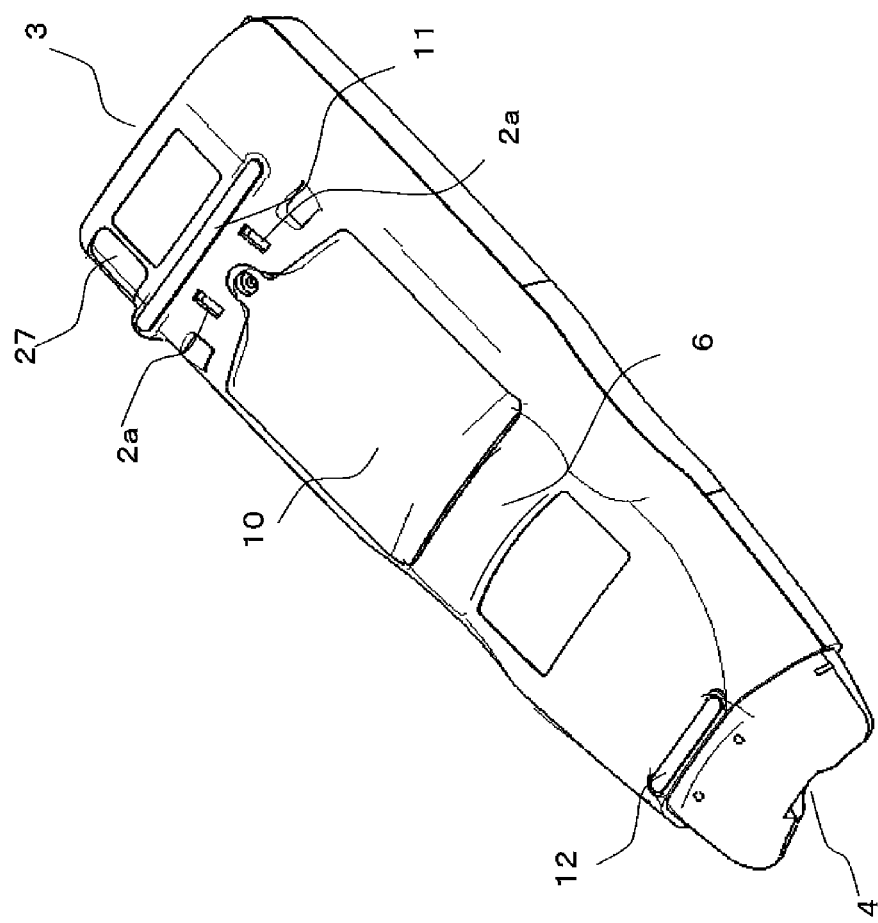
FIG. 5 is an oblique view of the rear side of the biological sample measuring device in FIG. 1.

As shown in FIGS. 4 and 5, a finger groove 6 that is recessed toward the main body case 1 side along the short-side direction of the main body case 1 is provided at a position that is closer to the sensor mounting portion 4 than the display section 5 on the rear side of the main body case 1.

The biological sample measuring device in this embodiment is designed so that the weight on the second end side (the sensor mounting portion 4 side) of the main body case 1 from the finger groove 6 is lighter than the weight on the first end side (the display section 5 side) of the main body case 1 from the finger groove 6.

As shown in FIGS. 2 and 3, an interface unit 7 is disposed at a location corresponding to the finger groove 6 on the front side of the main body case 1. Also, a sensor ejector lever 9 for ejecting a sensor 8 (see FIG. 13) from the sensor mounting portion 4 is disposed between the sensor mounting portion 4 and the interface unit 7 on the front side of the main body case 1.

As shown in FIGS. 4 and 5, a battery cover 10 is disposed between the data reader 3 and the finger groove 6 of the main body case 1 on the rear side of the main body case 1. A non-slip rubber foot 11 is disposed between the data reader 3 and the battery cover 10. A non-slip rubber foot 12 is disposed between the sensor mounting portion 4 and the finger groove 6.

With the biological sample measuring device of this embodiment configured as above, as shown in FIG. 4, a center of gravity position 1A of the device is set at a position that is closer to the data reader 3 than the finger groove 6 that is held by the measurement technician.

As shown in FIG. 3, the lateral width of the main body case 1 is greatest at the display section 5, and gradually decreases from the display section 5 toward the sensor mounting portion 4 side. That is, the design is such that the lateral width is at its least on the side of the sensor mounting portion 4.

Figure 6:
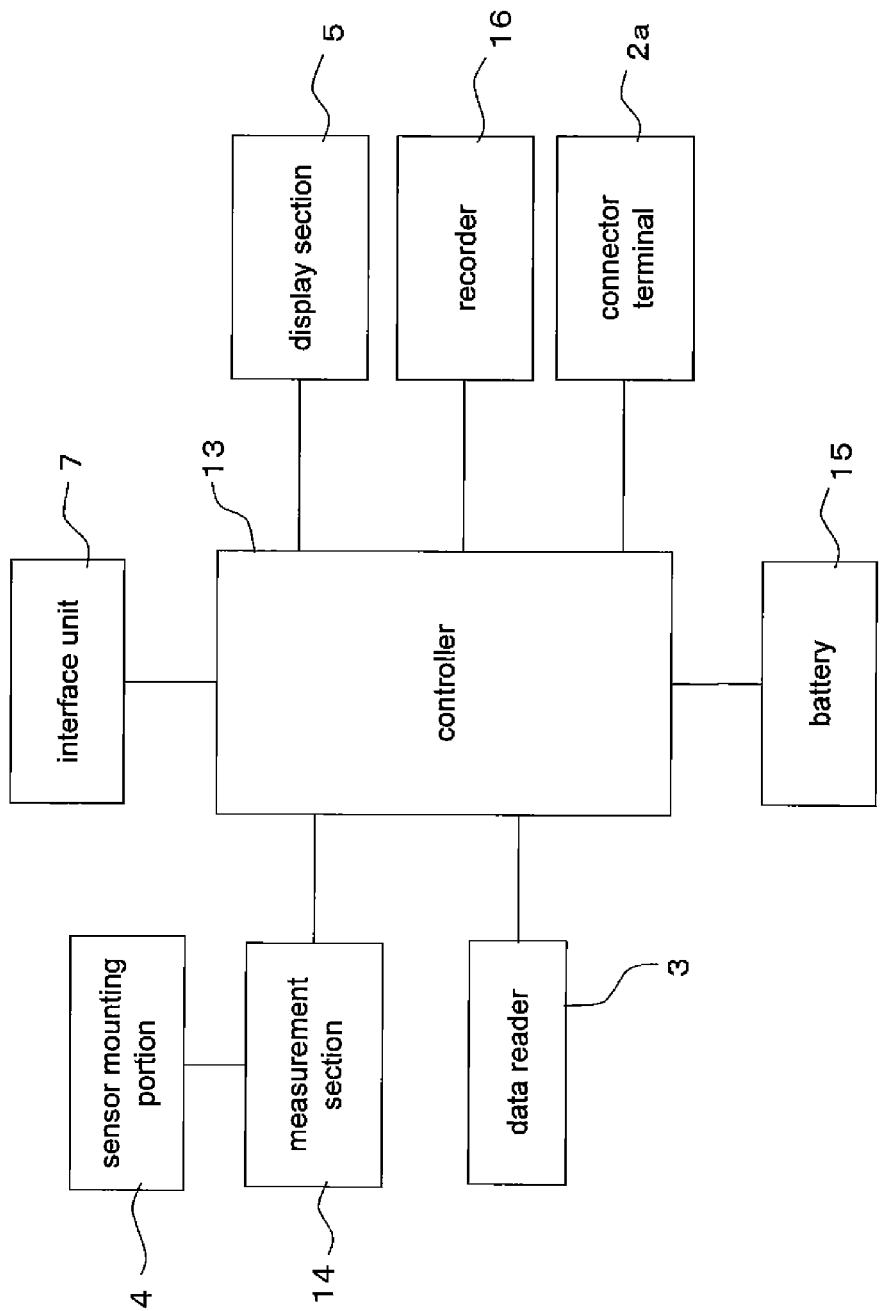
FIG. 6 is an electrical control block diagram of the biological sample measuring device in FIG. 1.

FIG. 6 is an electrical control block diagram of the biological sample measuring device.

With the biological sample measuring device in this embodiment, as is well known, a connector terminal 2a for connecting to the cradle 2, the data reader 3, the sensor mounting portion 4, and the display section 5 are connected to a controller 13. The sensor mounting portion 4 and the controller 13 are connected via a measurement section 14.

As shown in FIG. 6, a battery 15 is disposed inside the main body case 1 on the inner face side of the battery cover 10. A recorder 16 that records blood glucose levels and so forth is also disposed inside the main body case 1.

The procedure by which the biological sample measuring device of this embodiment is used to measure the blood glucose level of a patient in a hospital, for example, will be described through reference to FIGS. 7 to 14.

Figure 7:
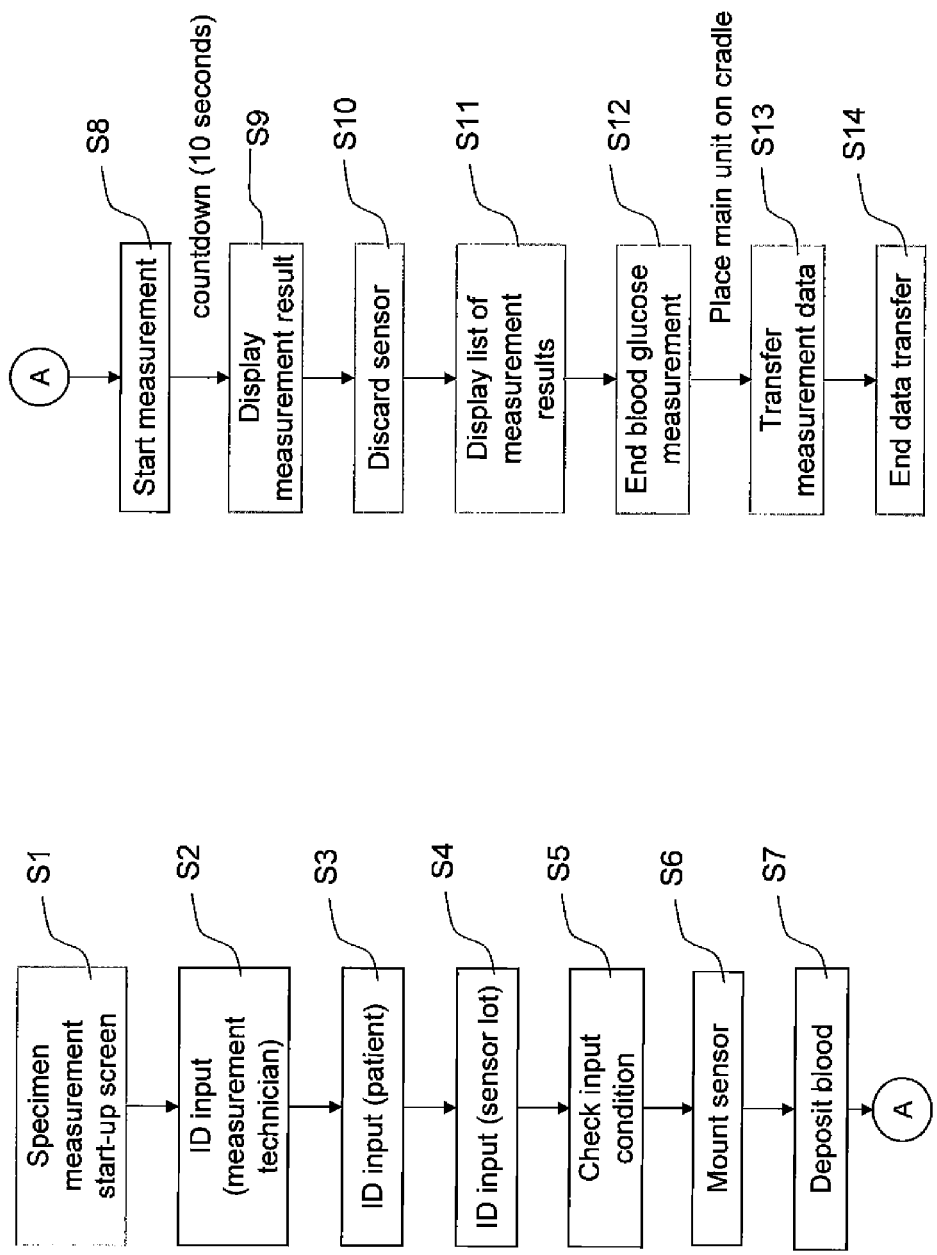
FIG. 7 is a flowchart of the operation of the biological sample measuring device in FIG. 1.

With the biological sample measuring device in this embodiment, as shown in the flowchart of FIG. 7, first the interface unit 7 is operated so as to display a specimen measurement start-up screen on the display section 5 (S1).

Figure 8:
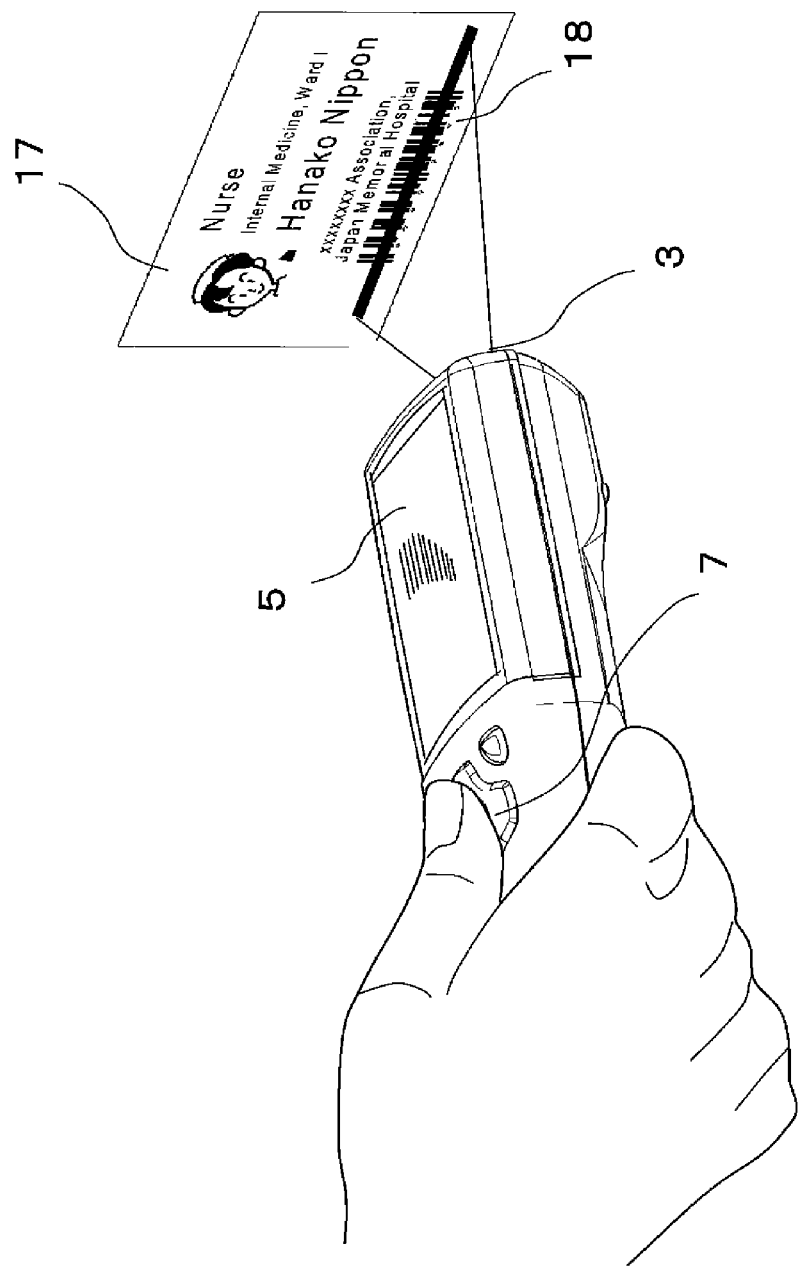
FIG. 8 is an oblique view of the usage state of the biological sample measuring device in FIG. 1.

Next, as shown in FIG. 8, the measurement technician (nurse) uses the data reader 3 to read ID data 18 displayed in barcode on a name tag 17 (S2). The ID data 18 is then recorded by the recorder 16.

Figure 9:
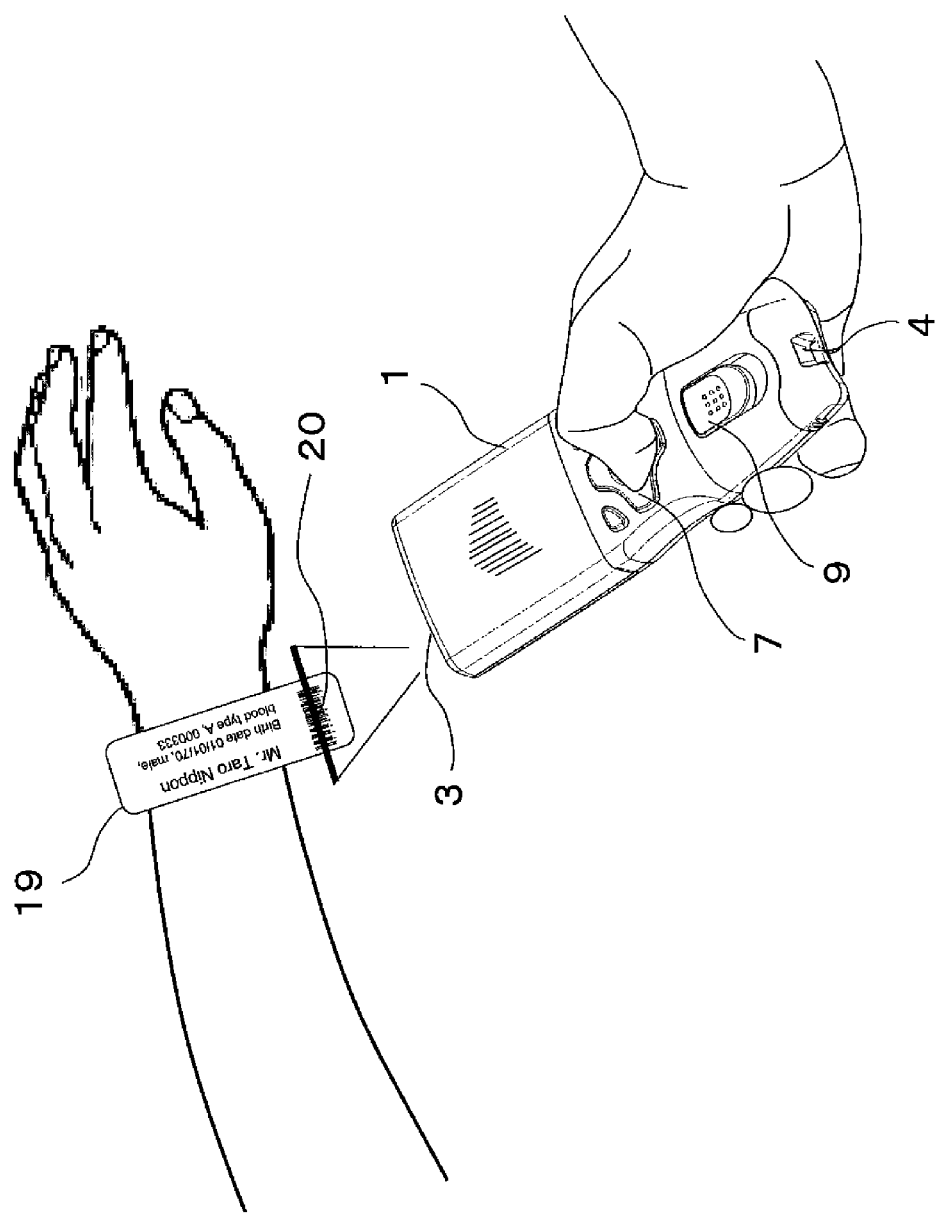
FIG. 9 is an oblique view of the usage state of the biological sample measuring device in FIG. 1.

Then, as shown in FIG. 9, ID data 20 displayed in barcode on a wristband 19 worn by the patient is read by the data reader 3 (S3). The ID data 20 is then recorded by the recorder 16.

Figure 10:
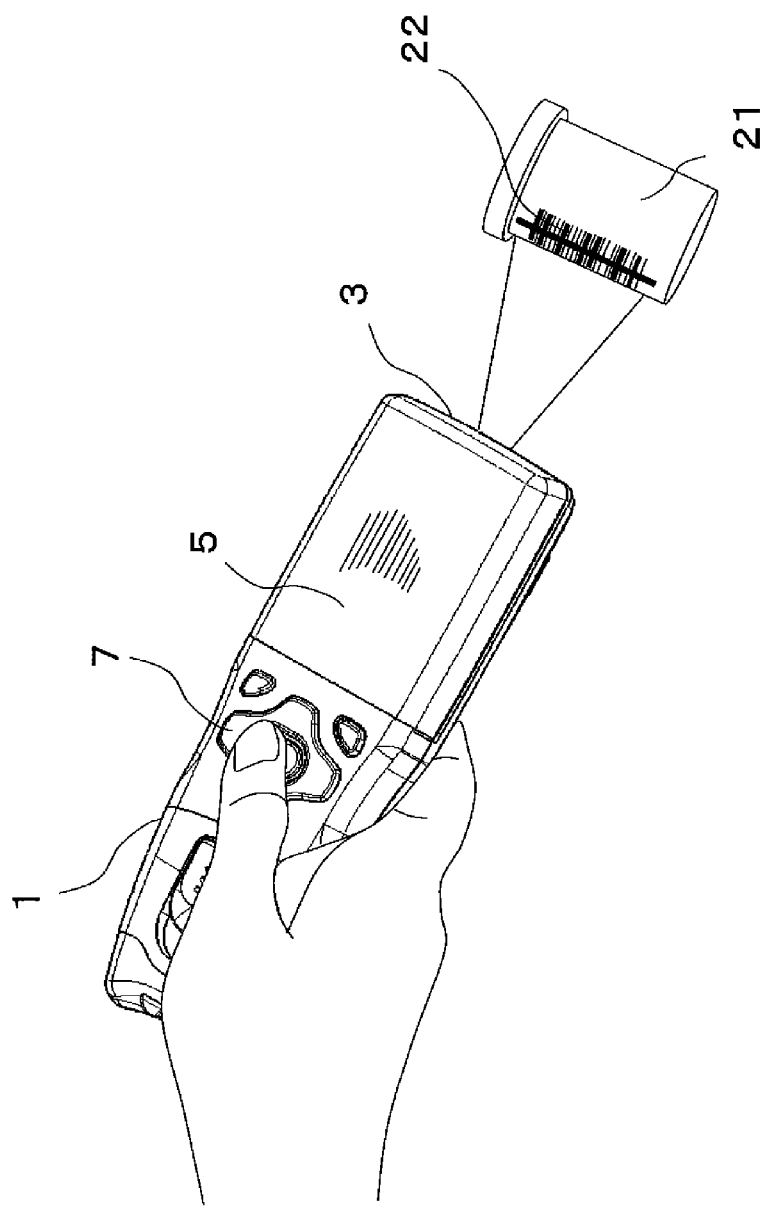
FIG. 10 is an oblique view of the usage state of the biological sample measuring device in FIG. 1.

Then, as shown in FIG. 10, the measurement technician (nurse) uses the data reader 3 to read ID data 22 displayed in barcode on a sensor bottle 21 containing a plurality of sensors 8 (see FIG. 13) (S4). The ID data 22 is then recorded by the recorder 16.

Figure 11:
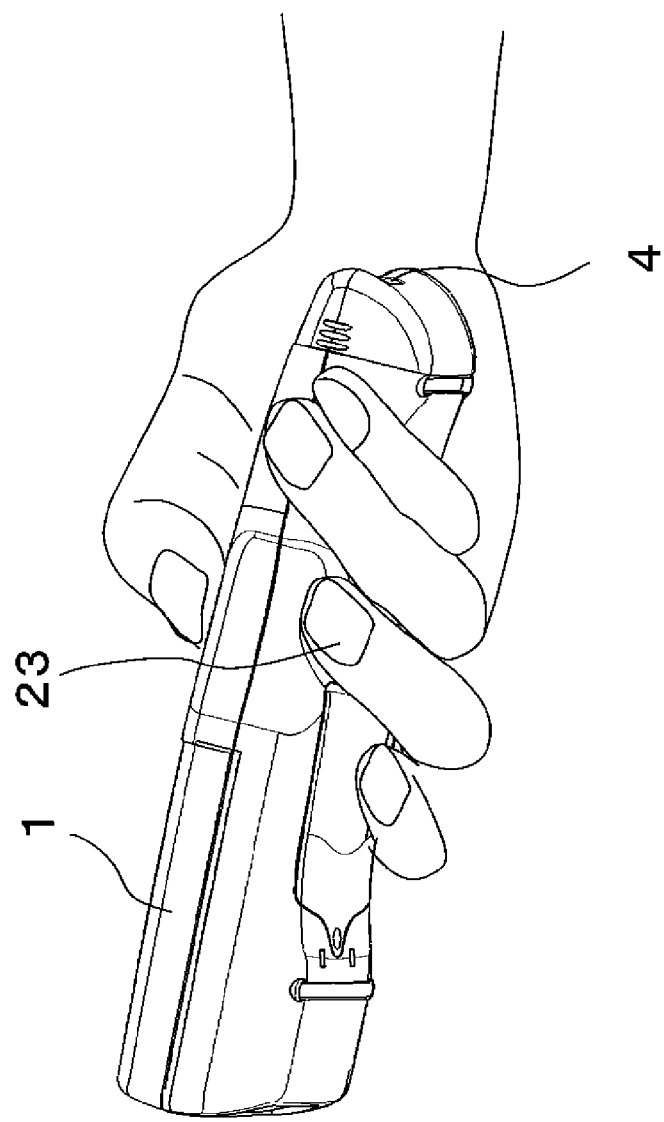
FIG. 11 is an oblique view of the usage state of the biological sample measuring device in FIG. 1.
Figure 12:
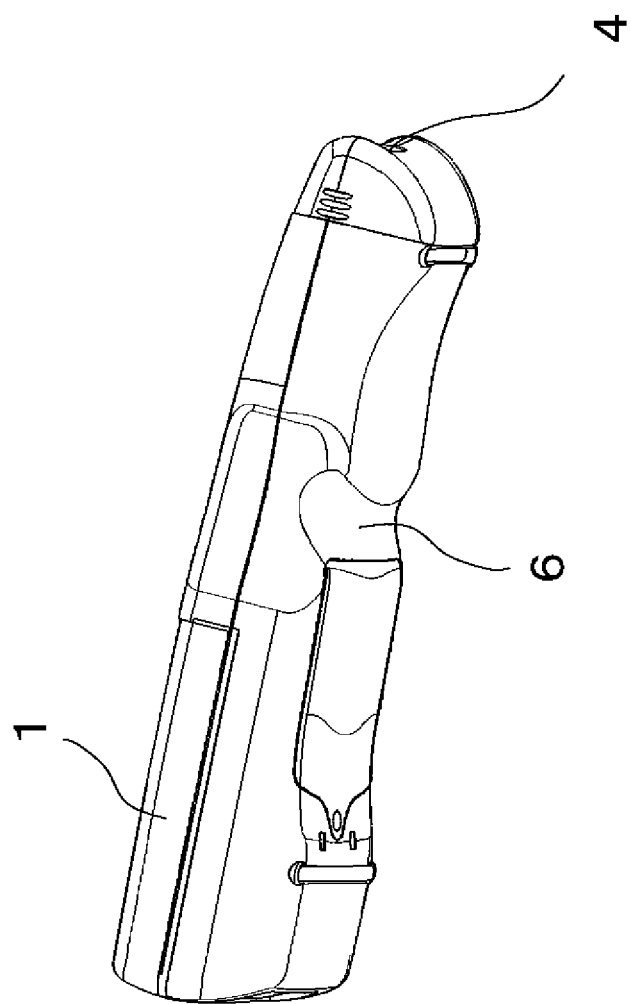
FIG. 12 is an oblique view of the usage state of the biological sample measuring device in FIG. 1.

As shown in FIGS. 11 and 12, during the reading of the ID data 18, 20, and 22 shown in FIGS. 8 to 10, the measurement technician (nurse) operates the interface unit 7 by putting his or her middle finger 23 into the finger groove 6 and holding the sensor mounting portion 4 side of the main body case 1.

As discussed above, the center of gravity position 1A of the main body case 1 is at a position closer to the data reader 3 than the finger groove 6, as shown in FIG. 4. Accordingly, during the operation shown in FIGS. 8 to 10, there is a certain amount of load exerted on the hand of the measurement technician (nurse).

With the biological sample measuring device in this embodiment, the measurement technician (nurse) holds the sensor mounting portion 4 side of the main body case 1 in a state in which his or her middle finger 23 is resting in the finger groove 6, and therefore even the operations shown in FIGS. 8 to 12 will not exert an especially heavy load on the measurement technician (nurse), allowing the work to be done with adequate dexterity.

Once the above operation is complete, the measurement technician (nurse) uses the interface unit 7 to display the ID data 18, 20, and 22 read from the recorder 16 on the display section 5, and checks whether or not the procedure so far has been carried out properly (S5).

Figure 13:
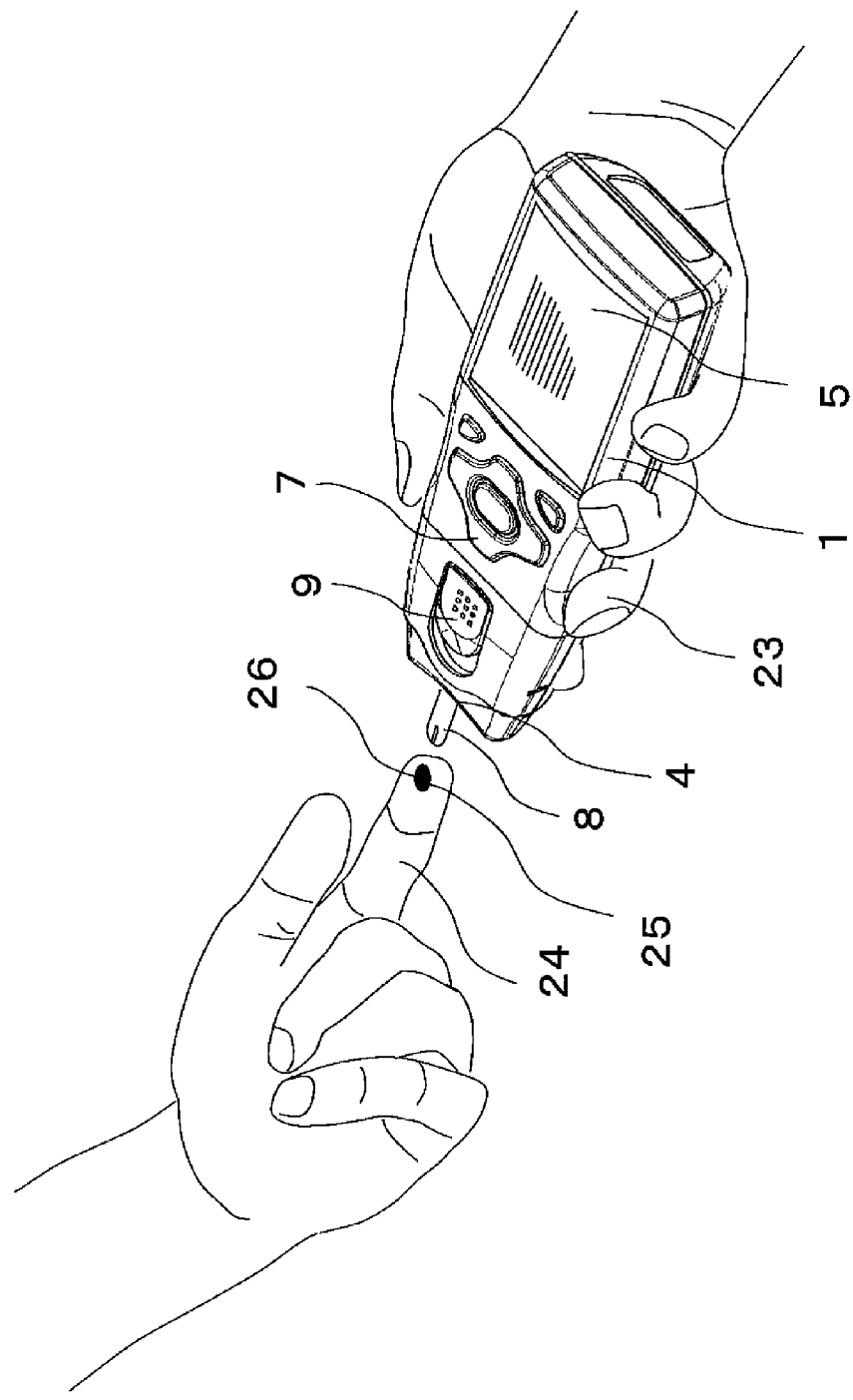
FIG. 13 is an oblique view of the usage state of the biological sample measuring device in FIG. 1.

Then, the measurement technician (nurse) takes out one of the sensors 8 (see FIG. 13) from the sensor bottle 21, and mounts it to the sensor mounting portion 4 as shown in FIG. 13. More specifically, the portion on the electrode side provided to the first end side of the sensor 8 is inserted into the sensor mounting portion 4 (S6).

As shown in FIG. 13, the insertion of the sensor 8 into the sensor mounting portion 4 and the subsequent work are carried out in a state in which the first end side (that is, the display section 5 side) of the main body case 1 is held.

More specifically, as shown in FIG. 13, for example, the measurement technician (nurse) carries out the work in a state in which the rear side on the first end side of the main body case 1 is resting on his or her palm, and the middle finger 23 is in the finger groove 6.

FIG. 13 shows a situation in which blood 26 is collected from a puncture 25 in the index finger 24 of the patient, and the blood glucose level of the patient is to be measured. Prior to this blood glucose level measurement, the measurement technician (nurse) performs a puncture operation on the puncture site 25 of the index finger 24 of the patient. Consequently, the blood 26 flows out of the puncture 25 in the index finger 24.

In this state, as shown in FIG. 13, the measurement technician (nurse) deposits the blood 26 on the distal end portion (second end side) of the sensor 8 (S7).

It is important to be careful here that the sensor 8 is not used so as to scoop up the blood 26 out of the puncture 25, or that the sensor 8 is not used so as press it against the blood 26 of the puncture 25. That is, it is important here that the blood 26 be deposited on the sensor 8, and that the blood 26 be drawn into the sensor 8 by the capillary action of the sensor 8.

In this embodiment, the configuration discussed above is employed so that the delicate operation of bringing the sensor 8 into contact with the blood 26 at the puncture 25 can be carried out simply.

Specifically, in this embodiment, the sensor mounting portion 4 is provided on the second end side of the main body case 1. The finger groove 6, which is formed in the short-side direction of the main body case 1, is provided at a position closer to the sensor mounting portion 4 than the display section 5 on the rear side of the main body case 1. Further, the design is such that the weight on the second end side of the main body case 1 from the finger groove 6 is lighter than the weight on the first end side of the main body case 1 from the finger groove 6.

Consequently, the job of depositing the blood 26 that has oozed out of the patient's puncture 25 onto the sensor mounted to the sensor mounting portion 4 is a job in which the lighter second end side of the main body case 1 is moved closer to the patient's puncture 25 in a state in which the user is holding the heavier first end side of the main body case 1.

Therefore, the delicate task of bringing the sensor 8 into contact with the patient's puncture 25 can be carried out easily. This effect is extremely important in places such as hospitals, where biological samples from numerous patients must be measured properly in a short time.

When the blood 26 is thus deposited on the sensor 8, measurement is begun at the measurement section 14 (S8), and after approximately 10 seconds, this measurement result is displayed on the display section 5 (S9).

This measurement result is recorded by the recorder 16 so that it is associated with the above-mentioned ID data 18, 20, and 22.

Next, the measurement technician (nurse) moves the sensor ejector lever 9 to the left in FIG. 13 (away from the second end side of the main body case 1), takes the sensor 8 off of the sensor mounting portion 4 to the outside of the main body case 1, and discards the sensor (S 10).

Next, the measurement technician (nurse) uses the interface unit 7 to display a list of the measurement data and ID data 18, 20, and 22 recorded by the recorder 16, on the display section 5 (S11). This completes the measurement of the blood glucose level (S12).

After this, when the main body case 1 is placed on the cradle 2 as shown in FIG. 1, the above-mentioned measurement data and ID data 18, 20, and 22 are transferred to the cradle 2 via a communication window 27 provided to the rear face of the main body case 1 shown in FIG. 5 (S13).

Then, this transferred measurement data and ID data 18, 20, and 22 are transferred from the cradle 2 to a host computer in a hospital (S 14).

Figure 14:
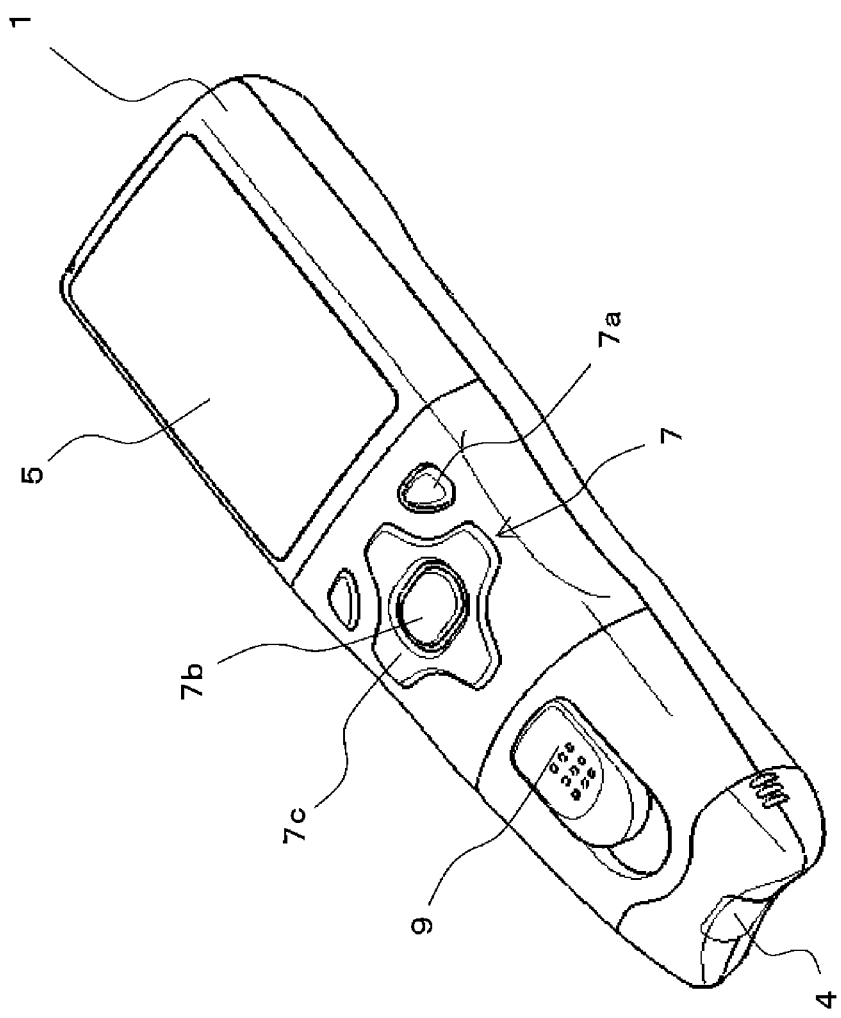
FIG. 14 is an oblique view of the configuration of the biological sample measuring device in FIG. 1.
Figure 15:
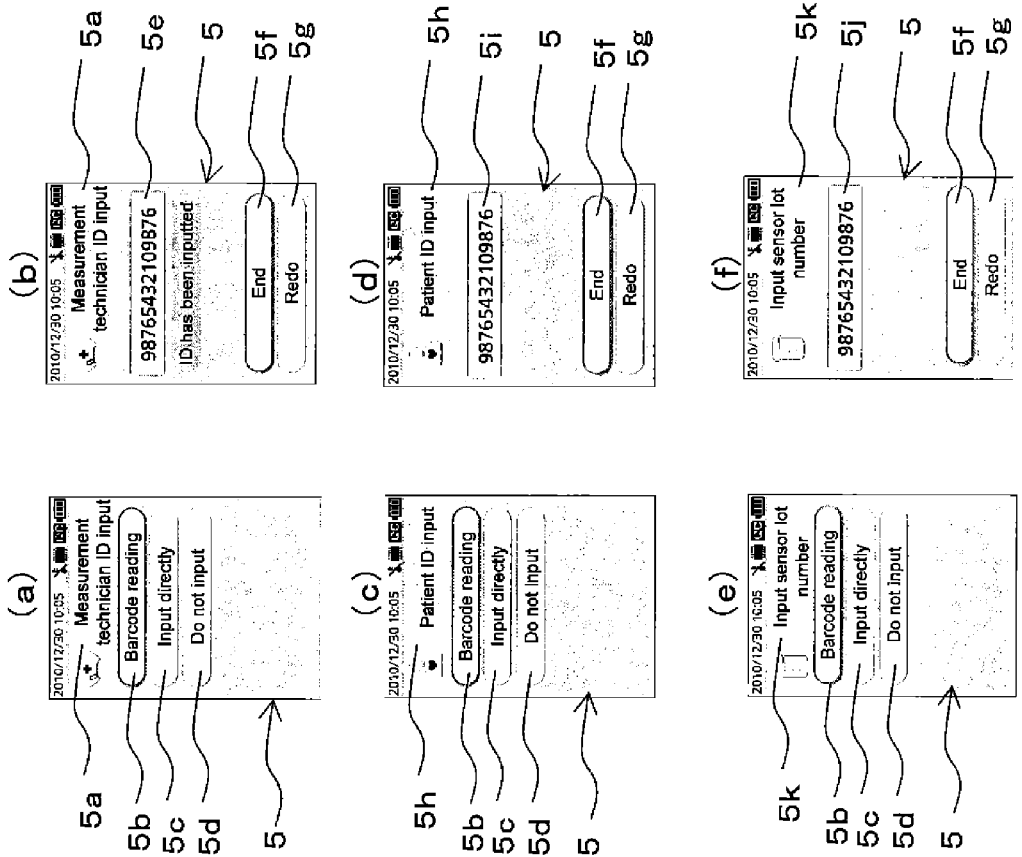
FIG. 15 is a diagram illustrating the operation of the biological sample measuring device in FIG. 14.

FIGS. 14 and 15 illustrate the operation of the data reader 3.

The data reader 3 is used during the measurement procedure shown in FIGS. 7 to 14 as discussed above.

To describe this point again, when a patient's blood glucose level is measured in a hospital, for example, first the interface unit 7 is used to display a specimen measurement start-up screen on the display section 5 (S1).

More specifically, when a power button 7a (part of the interface unit 7) is pressed, the screen shown in FIG. 15a is displayed. In FIG. 15a, a display 5a is shown at the top and is used to input the measurement technician ID. Below this is a display 5b for reading with a barcode reader, then a display 5c for inputting directly, and then a display 5d for not inputting.

When the power button 7a is pressed, the display 5b is selected.

Therefore, the measurement technician (nurse) inputs the measurement technician ID by barcode reader by pressing an enter key 7b (part of the interface unit 7).

More specifically, since a barcode reader constitutes the data reader 3, the ID data 18 displayed in barcode on the name tag 17 of the measurement technician (nurse) is then read by the data reader 3 as shown in FIG. 8 (S2). The ID data 18 for the measurement technician (nurse) thus read is displayed as ID data 5e on the display section 5 as shown in FIG. 15b. After the ID data 5e has been checked, the measurement technician (nurse) uses a cross key 7c (part of the interface unit 7) to select the display 5f for ending measurement technician (nurse) ID input, and then presses the enter key 7b to record the ID data 18 to the recorder 16.

The display 5g in FIG. 15b is used to re-read the ID data 18.

Next, as shown in FIG. 9, the measurement technician (nurse) uses the data reader 3 to read the ID data 20 displayed in barcode on the wristband 19 worn by the patient (S3).

In FIG. 15b, if the display 5f (indicating completion) is selected, then the display 5b (indicating barcode reading) is selected as shown in FIG. 15c. Here again, if the enter key 7b is pressed again, patient ID will be inputted by barcode reader.

As shown in FIG. 15c, the display 5h, which is used for inputting patient ID, is displayed at the top.

As shown in FIG. 15d, the patient ID data 20 that has been read is displayed as ID data 5i on the display section 5. The measurement technician (nurse) checks the ID data 5i, and then uses the cross key 7c (part of the interface unit 7) to select the display 5f to end patient ID input, and then presses the enter key 7b. This records the ID data 20 to the recorder 16.

Next, as shown in FIG. 10, the measurement technician (nurse) uses the data reader 3 to read the ID data 22 displayed in barcode on the sensor bottle 21 containing a plurality of sensors 8 (see FIG. 13) (S4). At this point, if the display 5f indicating completion in FIG. 15d is selected, then the display 5b indicating barcode reading in FIG. 15e is selected. Thus, here again, the enter key 7b is pressed once more to input the ID data 22 for the sensor bottle 21 by barcode reader.

In FIG. 15e, the display 5k, which is used to input the ID data 22 for the sensor bottle 21, is displayed at the top.

As shown in FIG. 15f, the ID data 22 for the sensor bottle 21 thus read is displayed as ID data 5j on the display section 5. The measurement technician (nurse) checks the ID data 5j, and then uses the cross key 7c (part of the interface unit 7) to select the display 5f to end the input of the ID data 22 for the sensor bottle 21, and presses the enter key 7b. This records the ID data 22 to the recorder 16.

As discussed above, with the biological sample measuring device in this embodiment, the ID data 18 for the measurement technician (nurse), the ID data 20 for the patient, and the ID data 22 for the sensor bottle 21 can be simply read by a barcode reader (the data reader 3). Furthermore, the content displayed on the display section 5 can be performed merely by pressing the enter key 7b located directly over the finger groove 6, so the operation can be carried out with the greatest of ease and with consistency.

FIGS. 16 to 19 illustrate the operation of forced resetting in the biological sample measuring device of this embodiment.

Specifically, a reset function is added to the biological sample measuring device in this embodiment.

Figure 16:
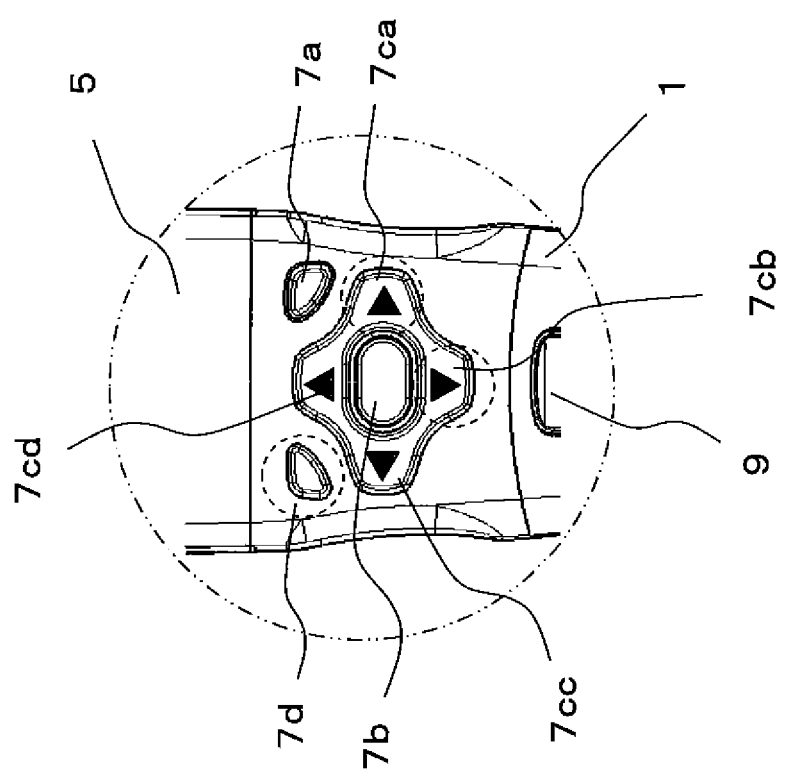
FIG. 16 is a plan view of the configuration near the interface unit of the biological sample measuring device in FIG. 1.

More specifically, as shown in FIG. 16, the cross key 7c has a cross key 7ca, a cross key 7cb, a cross key 7 cc, and a cross key 7cd, in that order starting from the power button 7a side.

A menu button 7d is provided on the opposite side from the power button 7a. The relative positional relations of these various parts, etc., will now be described.

As shown in FIG. 16, the enter key 7b is disposed in the approximate center of the biological sample measuring device. Around it are disposed the cross key 7ca, the cross key 7cb, the cross key 7 cc, and the cross key 7cd, evenly spaced apart by 90 degrees.

The cross key Ica and the cross key 7cc are disposed opposite each other with the enter key 7b in the middle. Similarly, the cross key 7cb and the cross key 7cd are disposed opposite each other with the enter key 7b in the middle. The power button 7a and the menu button 7d are disposed opposite each other with the cross key 7cd in the middle.

Figure 17:
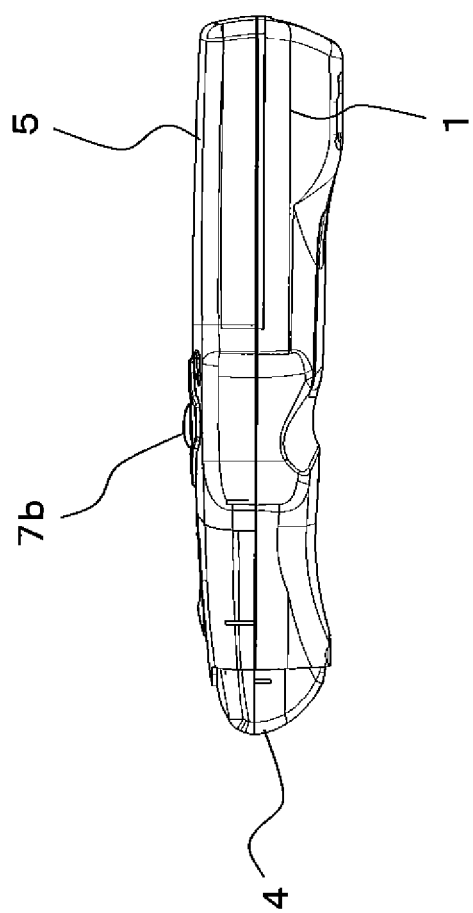
FIG. 17 is a front view of the biological sample measuring device in FIG. 16.

Of the above-mentioned power button 7a, enter key 7b, cross key 7ca, cross key 7cb, cross key 7cc, cross key 7cd, and menu button 7d, the enter key 7b protrudes the farthest from the surface of the main body case 1, as shown in FIG. 17.

Figure 19:
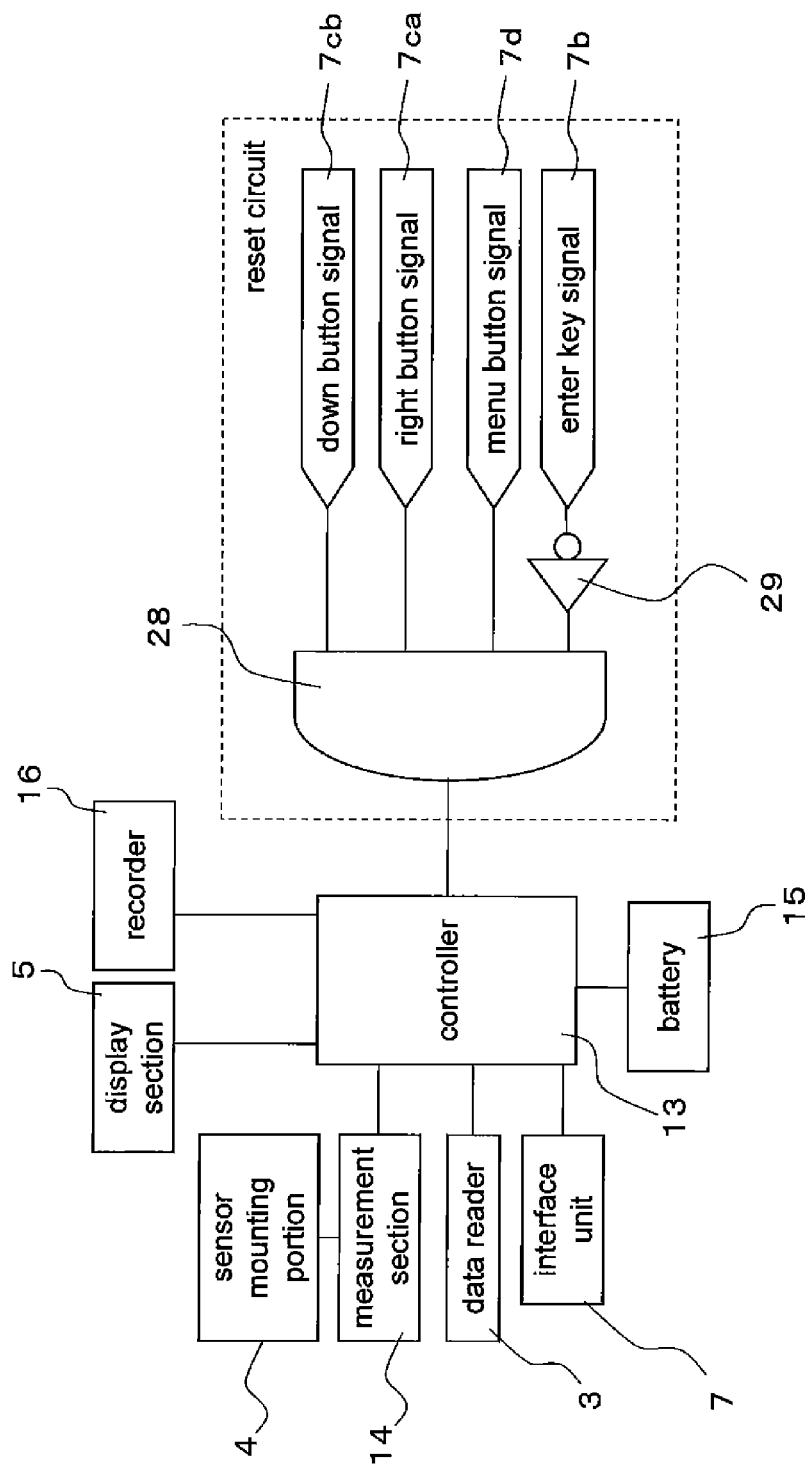
FIG. 19 is an electrical block diagram of the biological sample measuring device in FIG. 16.

With the biological sample measuring device in this embodiment, the above configuration and layout are in an electrically connected state, as shown in FIG. 19.

That is, the cross key 7ca, the cross key 7cb, and the menu button 7d are connected in series with an AND circuit 28. the enter key 7b is connected to the AND circuit 28 via an input inversion circuit 29. That is, a reset signal is outputted from the AND circuit 28 to the controller 13 when the cross key 7ca, the cross key 7cb, and the menu button 7d are pressed at the same time.

When a reset signal is inputted to the controller 13, the display is forcibly returned to the start-up screen shown in S1.

This reset operation is performed to return to a normal status when the program has malfunctioned. With a conventional biological sample measuring device, this was accomplished by inserting a pin into a small reset hole provided to the rear face of the main body case, but because this entails working with a small reset hole, it can be a difficult task for the measurement technician.

Figure 18:
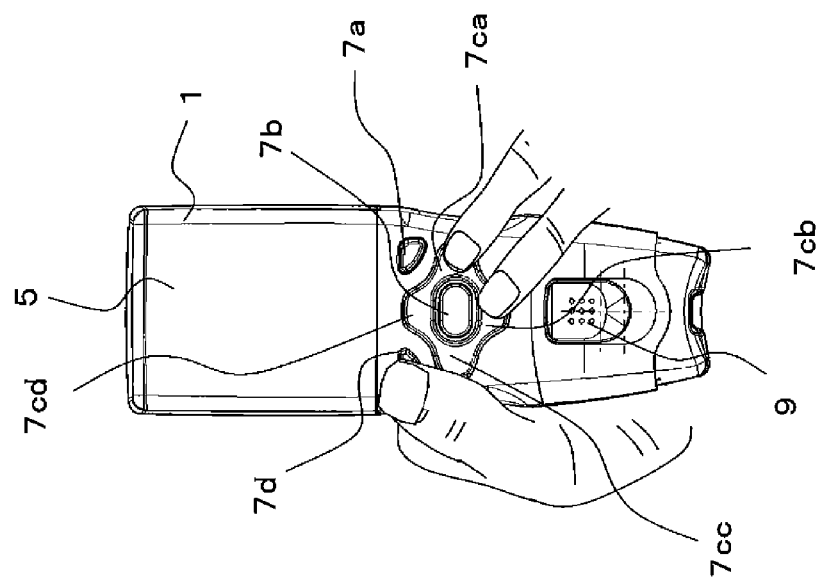
FIG. 18 is a plan view of the biological sample measuring device in FIG. 16.

In view of this, with the biological sample measuring device in this embodiment, as shown in FIG. 18, the reset operation can be simply performed by holding the main body case 1 in the left hand and using the right hand to reset the device, for example.

More specifically, with the left index finger in the finger groove 6, the menu button 7d is pressed with the left thumb, the cross key 7cb is pressed with the right index finger, and the cross key Ica is pressed with the right middle finger to perform the reset operation.

The downside of this simplicity is that a reset operation may be carried out accidentally, and to keep this from happening with the biological sample measuring device in this embodiment, the cross key 7ca, the cross key 7cb, and the menu button 7d are disposed around the outer periphery of the enter key 7b, while the enter key 7b, which is not related to resetting, protrudes farther from the surface of the main body case 1 than the cross key 7ca, the cross key 7cb, and the menu button 7d do.

Therefore, if the cross key 7ca, the cross key 7cb, and the menu button 7d are unintentionally and accidentally pressed, the enter key 7b that sticks out the farthest will always be pressed. Thus, at this point an inverted input will be made to the AND circuit 28 via the input inversion circuit 29 shown in FIG. 19. As a result, no reset signal will be inputted to the controller 13.

Thus, with the biological sample measuring device in this embodiment, the reset operation can be performed easily, and accidental resetting can be avoided. A highly reliable biological sample measuring device is therefore provided.

As discussed above, the biological sample measuring device in this embodiment is configured so that three buttons, namely, the cross key 7ca, the cross key 7cb, and the menu button 7d are pressed during the reset operation, but the reset operation may instead be performed by further pressing some other cross key, such as the cross key 7 cc.

The main thing here is that the reset operation can be carried out with both hands in a stable state in which the main body case 1 is held in one hand and the index finger is resting in the finger groove 6, for example, and that the places that are manipulated lie on both sides, sandwiching the enter key 7b that protrudes the most from the surface of the main body case 1.

Consequently, as long as the measurement technician (nurse) does not perform a reset operation accidentally, such as by placing some object on the surface of the main body case 1, unintentional resetting can be avoided.

Other Embodiments

An embodiment of the present invention was described above, but the present invention is not limited to or by the above embodiment, and various modifications are possible without departing from the gist of the invention.

(A)

In the above embodiment, an example was given in which the cross key 7ca, the cross key 7cb, the menu button 7d, and the enter key 7b were connected to the controller 13 via the AND circuit 28, the reset operation was performed when the cross key 7ca, the cross key 7cb, and the menu button 7d were all pressed at the same time, and inverted input was sent to the AND circuit 28 and the reset operation was not executed when the enter key 7b was pressed in addition to the above-mentioned keys, etc., but the present invention is not limited to this.

Figure 20:
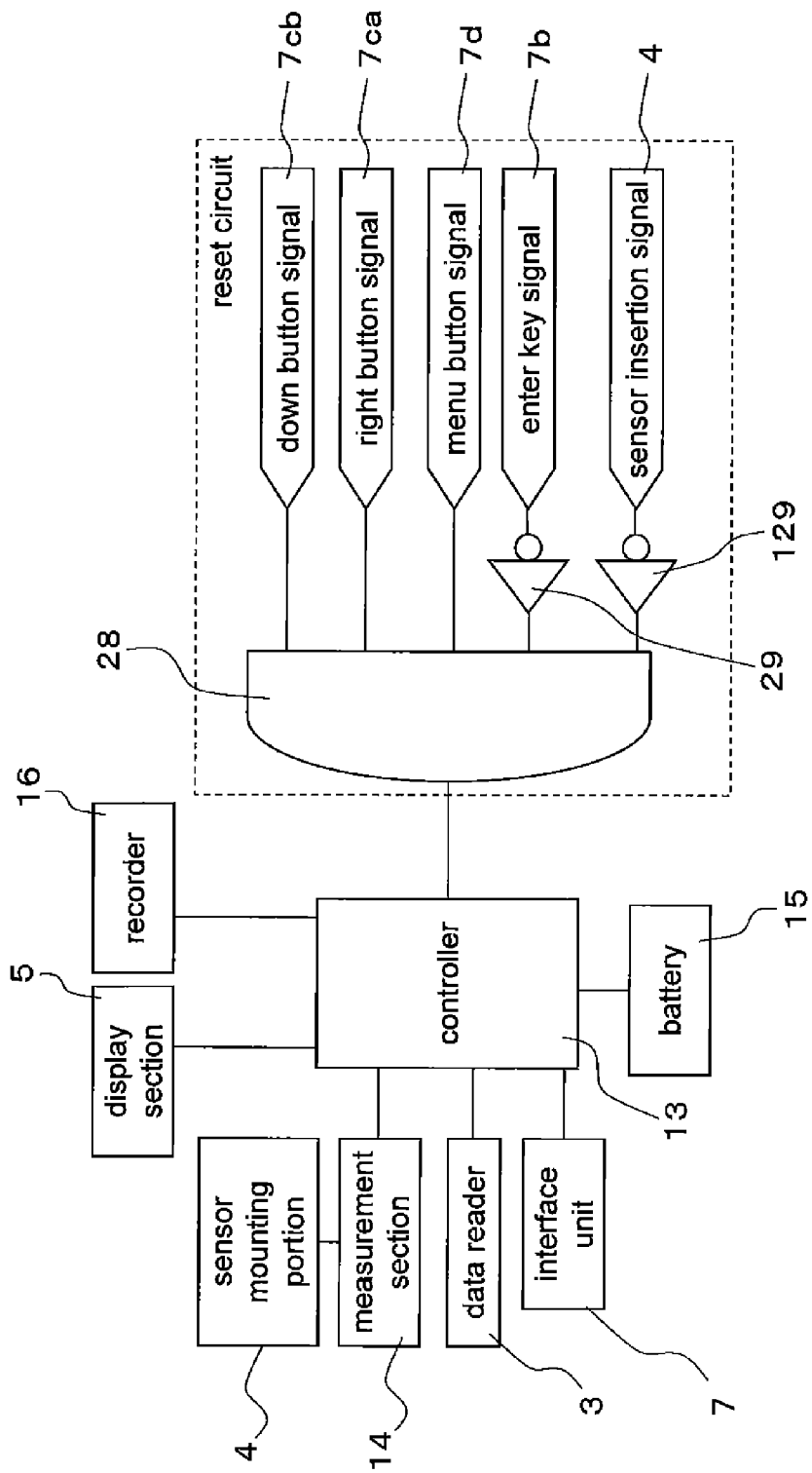
FIG. 20 is an electrical control block diagram of the biological sample measuring device pertaining to another embodiment of the present invention.

For example, as shown in FIG. 20, the configuration may be such that a sensor insertion signal that is sent from the sensor mounting portion 4 is inputted to a reset circuit.

In this case, if the set operation is performed in a state in which the sensor 8 has been mounted to the sensor mounting portion 4, an inverted input is sent from an input inversion circuit 129 to the AND circuit 28.

Consequently, execution of the reset operation can be avoided in a state in which the sensor 8 has been mounted to the sensor mounting portion 4. Thus, the reset operation will be possible only on the condition that no sensor insertion signal has not been received, that is, when no sensor has been mounted. Therefore, it is possible to effectively prevent a situation in which the measurement result is damaged as a result of the reset operation being executed in a state in which the sensor 8 has been mounted to the sensor mounting portion 4, such as during measurement.

In other words, since the measurement result is normally stored in a memory or the like once the measurement of a blood glucose level is finished, damage to data such as a measurement result can be effectively prevented by prohibiting a reset operation when a sensor is mounted.

INDUSTRIAL APPLICABILITY

As discussed above, the effect of the present invention is that accidental resetting can be prevented, and a biological sample measuring device that is more convenient to use can be provided, so it is expected to find application as a biological sample measuring device that measures blood glucose levels, lactic acid levels, and so forth in biological samples.

REFERENCE SIGNS LIST 1 main body case
1A center of gravity position
2 cradle
2A connector terminal
3 data reader
4 sensor mounting portion
5 display section
5a, 5b, 5c, 5d, 5f, 5g, 5h, 5k display
5e, 5i, 5j ID data
6 finger groove
7 interface unit
7a power button
7b enter key
7c cross key
7ca, 7cb, 7cc, 7cd cross key
7d menu button
8 sensor
9 sensor ejector lever
10 battery cover
11 rubber foot
12 rubber foot
13 controller
14 measurement section battery
16 recorder
17 name tag
18 ID data
19 wristband
20 ID data
21 sensor bottle
22 ID data
23 middle finger
24 index finger
25 puncture
26 blood
27 communication window
28 AND circuit
29 input inversion circuit
129 input inversion circuit

The invention claimed is:

1. A biological sample measuring device, comprising:
a main body case;
a data reader provided on a first end side in the lengthwise direction of the main body case;
a sensor mounting portion provided on a second end side that is on the opposite side from the first end in the lengthwise direction of the main body case;
a display section provided to the surface on the first end side of the main body case;
a finger groove provided at a position that is more to the sensor mounting portion side than the display section on the rear side of the main body case, and formed in the short-side direction of the main body case;
an interface unit that is provided at a position corresponding to the finger groove on the front side of the main body case, and that has an enter key and a plurality of keys or buttons disposed at a specific spacing around the outer periphery of the enter key so that the enter key protrudes the farthest on the front of the main body case; and
a controller that is connected to the interface unit and performs a reset operation when the plurality of keys or buttons are pressed at the same time.

2. The biological sample measuring device according to claim 1,
wherein the weight on the second end side of the main body case from the finger groove is lighter than the weight on the first end side of the main body case from the finger groove.

3. The biological sample measuring device according to claim 1,
wherein the interface unit has a cross key disposed around the outer periphery of the enter key, and a plurality of buttons disposed around the outer periphery of the cross key.

4. The biological sample measuring device according to claim 1,
wherein the controller performs the reset operation on the condition that a sensor insertion signal indicating that a sensor has been inserted into the sensor mounting portion has not been received.

5. The biological sample measuring device according to claim 4,
wherein the controller refuses to the reset operation when the reset operation is performed in a state in which the sensor insertion signal is being received.

6. A biological sample measuring device, comprising:
a main body case;
a data reader provided on a first end side in the lengthwise direction of the main body case;
a sensor mounting portion provided on a second end side that is on the opposite side from the first end in the lengthwise direction of the main body case;
a display section provided to the surface on the first end side of the main body case;
an interface unit having an enter key and a plurality of keys or buttons disposed at a specific spacing around the outer periphery of the enter key; and
a controller that is connected to the interface unit and performs a reset operation on the condition that a sensor insertion signal indicating that a sensor has been inserted into the sensor mounting portion has not been received, when the plurality of keys or buttons are pressed at the same time.

* * * * *